United States Patent
Bingley et al.

(10) Patent No.: US 9,820,699 B2
(45) Date of Patent: Nov. 21, 2017

(54) PROCESSING STATUS INFORMATION OF A MEDICAL DEVICE

(71) Applicant: KONINKLIJKE PHILIPS N.V., Eindhoven (NL)

(72) Inventors: Peter Bingley, Mierlo (NL); Angelique Carin Johanna Maria Brosens-Kessels, Eindhoven (NL); Jonathan David Mason, Waalre (NL); Jia Du, Waalre (NL); Paul Augustinus Peter Kaufholz, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 14/897,044

(22) PCT Filed: Jun. 12, 2014

(86) PCT No.: PCT/EP2014/062179
§ 371 (c)(1),
(2) Date: Dec. 9, 2015

(87) PCT Pub. No.: WO2014/202445
PCT Pub. Date: Dec. 24, 2014

(65) Prior Publication Data
US 2016/0113595 A1 Apr. 28, 2016

(30) Foreign Application Priority Data
Jun. 18, 2013 (EP) .................................. 13172407

(51) Int. Cl.
G08B 23/00 (2006.01)
A61B 5/00 (2006.01)
(Continued)

(52) U.S. Cl.
CPC ............ A61B 5/746 (2013.01); A61B 5/0002 (2013.01); G06F 19/3468 (2013.01);
(Continued)

(58) Field of Classification Search
CPC ....... A61B 5/002; A61B 5/746; A61B 5/0002; G06F 19/3406; G06F 19/3468; G08B 21/0453
(Continued)

(56) References Cited

U.S. PATENT DOCUMENTS 4,197,854 A 4/1980 Kasa
5,482,035 A 1/1996 Paloheimo
(Continued)

FOREIGN PATENT DOCUMENTS

WO 2012122002 A1 9/2012

OTHER PUBLICATIONS

Philips IntelliSpace Event Management.
(Continued)

Primary Examiner — Thomas Mullen

(57) ABSTRACT

A system (100) is provided for processing status information of a medical device (020-023). The medical device performs a medical function at a bedside of a patient and is arranged for generating an alarm signal (030) to alert a caregiver of the patient to an occurrence of an event which is associated with the performing of the medical function. A status interface (120) acquires a device signal (024) of the medical device, the device signal comprising status information which is indicative of a current status of the performing of the medical function. Moreover, an analysis subsystem (140) analyzes the status information to estimate an imminent occurrence of the event based on said current status, and a notification subsystem notifies the caregiver of the imminent occurrence away from the bedside of the patient of
(Continued)

the event by a generating a notification signal (162) for a notification device (060-064). The priority of notifying the caregiver is based on an estimate of whether the patient is asleep. The system enables the caregiver to be notified about the event ahead of time, i.e., before the event occurs and thus before the medical device generates an alarm signal. Advantageously, the patient is less disturbed by alarm signals during sleep.

12 Claims, 4 Drawing Sheets

(51) Int. Cl.
| | | |
|---|---|---|
| G06F 19/00 | (2011.01) | |
| G08B 21/04 | (2006.01) | |
| A61B 5/021 | (2006.01) | |
| A61B 5/024 | (2006.01) | |

(52) U.S. Cl.
CPC ........... *A61B 5/021* (2013.01); *A61B 5/02405* (2013.01); *A61B 5/4842* (2013.01); *A61B 5/7275* (2013.01); *A61B 2505/03* (2013.01); *A61B 2560/0266* (2013.01); *G06F 19/345* (2013.01); *G06F 19/3412* (2013.01); *G06F 19/3443* (2013.01); *G08B 21/0453* (2013.01)

(58) Field of Classification Search
USPC ..... 340/573.1, 539.12, 286.07; 600/300, 301
See application file for complete search history.

(56) References Cited

U.S. PATENT DOCUMENTS

| | | |
|---|---|---|
| 2006/0047538 A1 | 3/2006 | Condurso et al. |
| 2007/0255116 A1 | 11/2007 | Mehta et al. |
| 2007/0257788 A1 | 11/2007 | Carlson et al. |
| 2009/0128325 A1 | 5/2009 | Ivanov et al. |
| 2009/0284378 A1 | 11/2009 | Ferren et al. |
| 2009/0326340 A1 | 12/2009 | Wang et al. |
| 2011/0112442 A1 | 5/2011 | Meger et al. |
| 2011/0202495 A1 | 8/2011 | Gawlick |
| 2011/0291838 A1 | 12/2011 | Rantala |
| 2012/0126984 A1* | 5/2012 | Gilham .................. A61B 5/746 340/573.1 |
| 2012/0127103 A1 | 5/2012 | Qualey et al. |

OTHER PUBLICATIONS

Solution Brochure. http://www.healthcare.philips.com/us_en/products/hi_pm/products/IntelliSpace/Event_management.
Lotta Johansson, Ingegerd Bergbom and Berit Lindahl; "Meanings of Being Critically Ill in a Sound-Intensive ICU Patient Room—A Phenomenological Hermeneutical Study", The Open Nursing Journal, 2012, 6, 108-116, http://www.ncbi.nlm.nih.gov/pmc/articles/PMC3439833/pdf/TONURSJ-6-108.pdf.
Chan, Amanda L.; "Sleep Could Ease Delirium in ICU Patients, Study Finds", 2013, Source: http://www.huffingtonpost.com/2013/02/22/sleep-delirium-icu-recovery-patients_n_2727063.html.

* cited by examiner

PROCESSING STATUS INFORMATION OF A MEDICAL DEVICE

CROSS-REFERENCE TO PRIOR APPLICATIONS

This application is the U.S. National Phase application under 35 U.S.C. §371 of International Application No. PCT/EP2014/062179, filed on Jun. 12, 2014, which claims the benefit of European Patent Application No. 13172407.2, filed on Jun. 18, 2013. These applications are hereby incorporated by reference herein.

FIELD OF THE INVENTION

The invention relates to a system and a method for processing status information of a medical device performing a medical function at a bedside of a patient. The invention further relates to a computer program product comprising instructions for causing a processor system to perform said method.

BACKGROUND OF THE INVENTION

When a patient is admitted to a healthcare facility such as a hospital, the patient is frequently provided with one or more medical devices at his/her bedside that perform various medical functions. For example, an infusion pump at the bedside may infuse fluids, medication or nutrients into the patient's circulatory system. Another example is that a patient monitor may measure physiological data of the patient such as vital signs.

Such medical devices are frequently arranged for generating alarm signals to alert a caregiver of the patient to an occurrence of events which are associated with the performing of the medical function. For example, an infusion pump may be arranged for generating an alarm if a bag connected to the infusion pump runs empty. Accordingly, a nurse may be alerted to replace the empty bag. Another example is that a patient monitor may generate an alarm if the patient monitor determines that the state of a patient is deteriorating, e.g., by a heart rate of the patient becoming increasingly irregular. Yet another example is that the patient monitor may generate an alarm if a system malfunction occurred.

Such medical devices typically generate auditory alarms to alert a caregiver in the room of the patient or a caregiver being within hearing distance of the room. In fact, national regulations may stipulate that bedside medical devices generate auditory alarms for critical events. For that purpose, the medical device may comprise a loudspeaker.

Various systems are known for relaying such alarms to a mobile device of a caregiver to ensure communication of the alarm to the caregiver. For example, a system titled Philips IntelliSpace Event Management is said to have to following functionality, according to a document titled 'Solution brochure' downloaded on Jul. 06, 2013 from http://www.healthcare.philips.com/us_en/products/hi_pm/products/IntelliSpace/Event_management. When the primary caregiver is out of range or unavailable to answer an alert of a medical device, the product is said to enable a message to be routed to alternative caregivers or device(s). Moreover, a condition needing immediate attention can be escalated and routed to multiple qualified responders. User-controlled filters allow for customization of where critical messages should be routed. Alerts can be prioritized based on a clinical role of the caregiver. An alert delay can be configured to prevent a message from being sent to the caregiver's device if an alarm is cancelled before the end of the delay period.

US 2011/0202495 A1 provides a method and system for adjusting an alert rule used to indicate a status of a patient. It is said that some alert rules may also trigger calls to data mining models to apply predictions in real time by executing a prediction model.

US 2007/0257788 A1 provides a system and method for providing a safety alert for a device. In an embodiment where the device comprises an infusion pump, if an incorrect infusion rate was set, an alarm would be activated if the infusion rate had not been corrected within 30 seconds. The alarm would not be inactivated until the rate had been corrected and/or additional steps had been taken. An e-mail would also be sent to the pharmacist notifying him/her of an incorrect infusion rate.

However, the abovementioned systems do not address the following situation. When a patient is admitted to a healthcare facility, he/she frequently sleeps at the healthcare facility. It is well known that the quality of sleep is an important factor in the patient's healing process. When the patient sleeps well, the recovery time, e.g., after a surgery, is frequently shortened. Unfortunately, many patients in healthcare facilities experience insufficient quality of sleep. A reason for this is that the healthcare environment is quite different from what patients are used to at home. In particular, ambient factors such as light levels and sound levels can play a role in keeping patients awake.

SUMMARY OF THE INVENTION

The inventors have recognized that alarms generated by bedside medical devices are particularly disturbing to a good quality of sleep. For example, an auditory alarm may cause patients which are already asleep to be woken up. Moreover, some medical devices, such as infusion pumps, are typically not connected to a nurses' central station. As a result, the patient has to fully wake up in order to press the nurse call button and wait for the nurse to attend to the medical device, typically with the alarm still sounding. With multiple patients per room and multiple alarms being generated each night, this has a detrimental effect on the sleep quality of patients, which in turn has a negative impact on their recovery.

Although the Philips IntelliSpace Event Management system enables alarms to be routed to alternative caregivers or device(s) to ensure communication of the alarm, the alarm is still generated at bedside. Accordingly, the patient is still disturbed by the alarm.

It would be advantageous to obtain a system or method which is able to reduce or which entirely avoids patients being disturbed by alarms that are generated by the medical devices at their bedside, in particular when the patients are sleeping.

To better address this concern, a first aspect of the invention provides a system for processing status information of a medical device performing a medical function at a bedside of a patient, the medical device being arranged for generating an alarm signal which is perceivable at the bedside of the patient to enable alerting a caregiver of the patient to an occurrence of an event which is associated with the performing of the medical function, the system comprising:
 a status interface for acquiring a device signal of the medical device, the device signal comprising status information which is indicative of a current status of the performing of the medical function;

an analysis subsystem for analyzing the status information to estimate an imminent occurrence of the event based on said current status; and a notification subsystem for notifying the caregiver of the imminent occurrence of the event away from the bedside of the patient by a generating a notification signal for a notification device, the notification subsystem being arranged for i) determining a priority of the notifying of the caregiver based on estimating whether the patient is asleep, and ii) effecting the notifying of the caregiver based on the priority.

In a further aspect of the invention, a mobile device is provided for performing a medical function at a bedside of a patient, the medical device being arranged for generating an alarm signal which is perceivable at the bedside of the patient to enable alerting a caregiver of the patient to an occurrence of an event which is associated with the performing of the medical function, the medical device comprising the system set forth.

In a further aspect of the invention, a method is provided for processing status information of a medical device performing a medical function at a bedside of a patient, the medical device being arranged for generating an alarm signal which is perceivable at the bedside of the patient to enable alerting a caregiver of the patient to an occurrence of an event which is associated with the performing of the medical function, the method comprising:

acquiring a device signal of the medical device, the device signal comprising status information which is indicative of a current status of the performing of the medical function;

analyzing the status information to estimate an imminent occurrence of the event based on said current status; and notifying the caregiver of the imminent occurrence of the event away from the bedside of the patient by generating a notification signal for a notification device, said notifying comprising i) determining a priority of the notifying of the caregiver based on estimating whether the patient is asleep, and ii) effecting the notifying of the caregiver based on the priority.

In a further aspect of the invention, a computer program product is provided comprising instructions for causing a processor system to perform the method set forth.

The above measures provide a system and method for processing status information of a medical device. The medical device is provided at a bedside of the patient, i.e., at or nearby the patient's bed in a room of a healthcare facility. Such a medical device is frequently also referred to as a bedside medical device, and includes medical devices such as infusion pumps, patient monitors, drainage systems, enteral feeding tubes, etc. The medical device performs a medical function with respect to the patient in that it is involved in the monitoring or treatment of the patient. The medical device is able to generate an alarm signal, such as an auditory alarm, so as to alert a caregiver of the patient. The alarm signal is generated by the medical device to be clearly perceivable at the bedside of the patient, as is typically the case due to regulation. The medical device generates the alarm signal to notify the caregiver of an occurrence of an event which is associated with the performing of the medical function. For example, the medical device may generate an alarm if a bag runs empty, a patient's vital sign exceeds a threshold, etc. The alarm may also be related to a malfunction of the medical device which impairs or endangers the performing of the medical function. For example, the medical device may generate an alarm if a battery malfunctions.

The medical device makes available a device signal which comprises status information which is indicative of a current status of the performing of the medical function. Here, the term current status refers to a state of the performing of the medical function at an approximate time of providing the device signal, i.e., which is neither a historic state nor a future state. The status information relates to the performing of the medical function and as such may relate to a state of the medical device itself in respect of the medical function, i.e., constitute technical status information, as well as to a state of the patient as measured, controlled or otherwise influenced by the medical function, i.e., constitute patient status information. For example, an infusion pump may make available a device signal which indicates that the infusion pump is operating at a given infusion speed, that a new bag has been placed, etc. In particular, the device signal may make the kind of status information available which is typically logged in an internal electronic log of the medical device. According to the present invention, a status interface is provided which acquires the device signal of the medical device. For example, the status interface may receive the device signal directly from the medical device, e.g., via a network interface. However, the device signal may equally be provided on a display of the medical device for display to the caregiver, and the status interface may acquire the device signal by means of analyzing a camera image which shows the display and thus the device signal provided thereon. Furthermore, an analysis subsystem is provided which analyzes the status information contained in the device signal to estimate an imminent occurrence of the event based on the current status of performing the medical function. Accordingly, the analysis subsystem determines whether the information provided by the device signal indicates that an event will occur in the near future for which the medical device will generate an alarm.

A notification subsystem is provided which generates a notification signal for a notification device in case the analysis subsystem has estimated that the event will occur in the near future. The notification device is a device which is observable by the caregiver away from the bedside of the patient. For example, the notification device may be constituted by a mobile phone of the caregiver or by a call light above the door of the patient room.

The notification subsystem estimates how important or urgent it is to notify the caregiver of the imminent occurrence of the events, and carries out the actual notifying of the caregiver based on said estimate. For example, if the notification subsystem estimates that the notifying of the caregiver has a high priority, e.g., based on a type of the event, the notification subsystem may notify the caregiver of the imminent event without delay. In particular, the notification subsystem is arranged for determining the priority based on estimating whether the patient is asleep. If the patient is asleep, it is especially desirable to avoid the patient being distracted by alarm signals generated by medical devices. Accordingly, it is typically more important for the caregiver to be notified of events ahead of time when the patient is asleep. To enable the priority of notifying the caregiver to be suitably determined, the notification subsystem estimates whether the patient is asleep. Advantageously, the system is enabled to prioritize notifications for the caregiver.

The above measures have the following effect. By acquiring the device signal of the medical device, the system is provided with status information of the medical device, and in particular with status information associated with the performing of the medical function. The inventors have recognized that such status information is frequently indicative of events which will occur in the near future, and which will, upon the occurrence of such an event, cause the medical device to generate an alarm signal. For example, if the status information indicates that the infusion pump is currently operating at a high infusion speed, the analysis subsystem can determine that a bag of a standard size will run empty soon and which will cause the infusion pump to generate an alarm on the empty bag. By estimating such an imminent occurrence of the event based the current status, the system is enabled to notify the caregiver of the imminent occurrence of the event. By generating a notification signal for a notification device which is observable by the caregiver away from the bedside of the patient, the caregiver is enabled to learn about the imminent event without having to be at the bedside of the patient and without the notification signal disturbing the patient.

Accordingly, the caregiver is notified about the event ahead of time, i.e., before the event occurs and thus before the medical device generates an alarm signal to alert the caregiver to the occurrence of the event. Advantageously, the caregiver can act to prevent the event from occurring. For example, the caregiver may replace the bag of the infusion pump before it runs empty. Advantageously, by notifying the caregiver about such events ahead of time, fewer alarm signals will be generated. Advantageously, by determining the priority of the notifying based on an estimate whether the patient is asleep, the patient is less disturbed during sleep. Advantageously, the patient's recovery time is shortened. Advantageously, family and friends of the patients are less worried since fewer alarm signals are generated. Caregivers may also be less stressed as the fewer alarm signals lead to fewer interruptions in their normal routine and to less urgent attending of such alarms.

Optionally, the notification subsystem is arranged for estimating whether the patient is asleep based on at least one of the group of: physiological data as obtained from a patient monitor, time data indicating a time of day, and light data being indicative of an amount of light in a room of the patient. Physiological data such as heart rate or electrical activity along the scalp of the patient is well suited for estimating whether the patient is asleep, as also known per se from the field of polysomnography. Furthermore, both the time of day and the amount of light in the room of the patient provide simple yet effective estimate of whether the patient is asleep. Advantageously, the notification subsystem uses one or more of the aforementioned techniques to more accurately estimate whether the patient is asleep.

Optionally, the notification subsystem is arranged for delaying or discarding said notifying if the priority does not exceed a threshold. Accordingly, the notification subsystem is enabled to omit notifying the caregiver if the priority is relatively low. For example, if the caregiver has been already notified of the occurrence of a related event, the notification subsystem may chose to entirely omit to notify the caregiver in this case. Advantageously, the caregiver is not distracted by notifications which have a low priority.

Optionally, the analysis subsystem is arranged for i) tracking the status information over time to obtain a time series of status information, and ii) estimating the imminent occurrence of the event based on an extrapolation of the time series of status information. The analysis subsystem thus uses, in addition to status information which is indicative of the current status of the performing of the medical function, also status information which is indicative of one or more past statuses. Accordingly, the analysis subsystem is provided with information how the performing of the medical function changes over time, e.g., how rapidly and in which direction. By extrapolating the time series of status information, the analysis subsystem makes use of the changes in the performing of the medical function over time to predict the imminent occurrence of the event. For example, if each status information is indicative of a blood pressure of the patient, the analysis subsystem is enabled to estimate if there appears to be a trend in the blood pressure over time, and if so, if this trend is expected to result in the blood pressure reaching a value with would cause the medical device to generate an alarm signal to alert the caregiver. Advantageously, the analysis subsystem is enabled to accurately estimate the imminent occurrence of the event.

Optionally, the analysis subsystem is arranged for estimating a time of the imminent occurrence of the event, and the notification subsystem is arranged for generating the notification signal to notify the caregiver of said time. The caregiver is thus not only notified of the imminent occurrence of the event, but also on the time of the occurrence. Advantageously, the caregiver is enabled to timely act so as to prevent the event from occurring. Advantageously, the caregiver is enabled to plan in time when he/she needs to act upon the notification so as to prevent the imminent occurrence of the event.

Optionally, the status interface is further arranged for acquiring physiological data from a patient monitor of the patient, and the analysis subsystem is arranged for estimating the imminent occurrence of the event further based on the physiological data. The analysis subsystem is thus provided with physiological data of the patient as measured by a patient monitor. Such physiological data may include, e.g., measured vital signals of the patient. The analysis subsystem uses the physiological data as additional input in estimating the imminent occurrence of the event. Advantageously, the physiological data enables the analysis subsystem to more accurately estimate the imminent occurrence of the event in situations where the physiological data supplements the status information.

Optionally, the notification subsystem is arranged for generating the notification signal for a mobile notification device of the caregiver. The term mobile notification device refers to a mobile device which is able to notify the caregiver, e.g., by being able to receive and present text messages to the caregiver. Examples of such mobile notification devices include mobile phones, e.g., Smartphones, tablets and pagers. By generating the notification signal for the mobile notification device of the caregiver, the likelihood of the caregiver observing the notification in a timely manner is increased.

Optionally, the notification subsystem is arranged for generating the notification signal for effecting a non-auditory notification of the caregiver. By notifying the caregiver in a non-auditory manner, e.g., using light or vibration, the likelihood of the notification disturbing the patient is reduced, in particular if the patient is asleep. Advantageously, such non-auditory notification of the caregiver is less likely to disturb the patient compared to the auditory alarm signals as typically generated by medical devices. Advantageously, the notification device can be arranged in or nearby the patient's room.

Optionally, the notification device comprises a light source, and the notification subsystem is arranged for generating the notification signal for effecting the notification of the caregiver via the light source. The caregiver is thus notified via a light signal. Advantageously, if the light source is arranged at or near an entrance of the room of the patient, the caregiver can easily observe any notifications while passing by the room.

It will be appreciated by those skilled in the art that two or more of the above-mentioned embodiments, implementations, and/or aspects of the invention may be combined in any way deemed useful.

Modifications and variations of the method and/or the computer program product, which correspond to the described modifications and variations of the system, can be carried out by a person skilled in the art on the basis of the present description.

The invention is defined in the independent claims. Advantageous yet optional embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
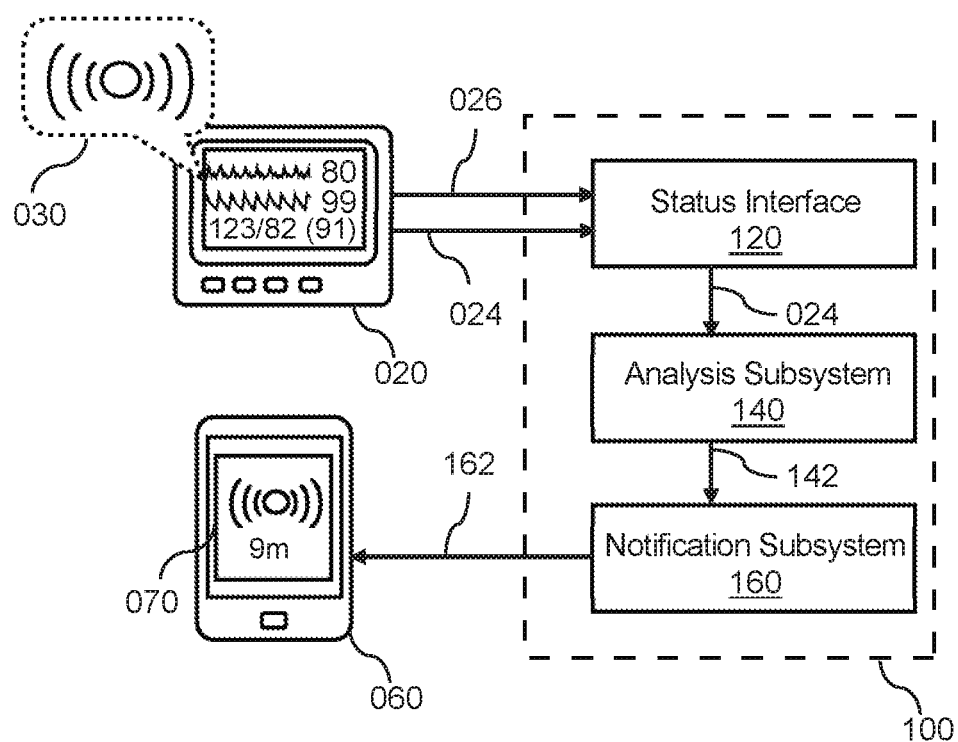
FIG. 1 shows a system for processing status information of a medical device, the system providing a notification signal to a notification device to notify a caregiver of an imminent event which is estimated to occur based on an analysis of the status information.

FIG. 1 shows a system 100 for processing status information of a medical device 020 which performs a medical function at a bedside of a patient. The medical device 020 is arranged for generating an alarm signal 030 which is perceivable at the bedside of the patient to enable alerting a caregiver of the patient to an occurrence of an event which is associated with the performing of the medical function. The alarm signal 030 may be a disturbing alarm signal such as an auditory alarm signal. The alarm signal 030 is indicated in FIG. 1 by a callout box which is dashed to denote that the alarm signal 030 is a possible future alarm signal 030, i.e., the medical device 020 is not yet sounding the auditory alarm. By way of example, the medical device 020 is shown to be a patient monitor 020 for measuring vital signals of the patient. The system 100 comprises a status interface 120 for acquiring a device signal 024 of the medical device, with the device signal 024 comprising status information which is indicative of a current status of the performing of the medical function. For example, the status interface 120 may obtain the device signal 024 in the form of a network message via a local area network. The network message may indicate that an internal battery of the medical device 020 is running empty. Another example is that the network message may indicate that a consistently irregular cardiac rhythm of the patient has been measured.

The system 100 further comprises an analysis subsystem 140 for analyzing the status information to estimate an imminent occurrence of the event based on said current status. Here, the term imminent refers to a near future, e.g., as measured in minutes rather than days. For example, the analysis subsystem 140 may determine that since a warning limit has been reached for a SpO2 reading of the patient, it is likely that the medical device 020 will sound an alarm signal 030 in 5 minutes, e.g., based on the type of warning limit. The analysis system 140 is shown to receive the device signal 024 which comprises the status information from the status interface 120. Alternatively, the analysis subsystem 140 may directly receive the status information from the status interface 120, e.g., after the status interface 120 processed the device signal 024 to obtain the status information. Although not shown in FIG. 1, the analysis subsystem 140 may make use of internal or external data which aids in the analysis or interpretation of the status information, i.e., interpretation data such as medical device information, medical textbooks, medical guidelines, etc. However, this is not a limitation, in that the analysis subsystem 140 may equally be arranged to estimate the imminent occurrence of the event solely based on the status information itself, e.g., in cases where the status information is sufficiently indicative of said imminent occurrence.

The system 100 further comprises a notification subsystem 160 for notifying the caregiver of the imminent occurrence of the event away from the bedside of the patient by a generating a notification signal 162 for a notification device 060. To inform the notification subsystem 160 of the imminent occurrence of the event, the analysis subsystem 140 is shown to provide event data 142 to the notification subsystem 160. FIG. 1 shows the notification device 060 being a mobile notification device of the caregiver, in particular a mobile phone. In this example, the notification signal 162 may be provided to the mobile phone 060 via wireless communication techniques. However, this is not a limitation, in that the notification device may also be a stationary device and/or be connected to the system 100 via wire.

FIG. 1 shows a result of the notification subsystem 160 generating the notification signal 162 for the notification device 060 and providing the notification signal 162 to the notification device 060, namely that the caregiver is presented with a notification 070 showing a graphical representation of the alarm signal 030. FIG. 1 further shows an optional aspect of the present invention, in that the notification also indicates an estimated time of the imminent occurrence of the event, i.e., of the imminent event, namely by indicating the remaining time until the event, being here 9 minutes.

An operation of the system 100 may be briefly explained as follows. The medical device 020 performs the medical function at the bedside of the patient. The status interface 120 acquires the device signal 024 of the medical device. The device signal 024 comprises status information which is indicative of the current status of the performing of the medical function by the medical device 020. The analysis subsystem 140 analyzes the status information to estimate the imminent occurrence of the event based on said current status. The notification subsystem 160 notifies the caregiver of the imminent occurrence of the event by generating the notification signal 162 for the notification device 060 and providing, or making available, the notification signal 162 to the notification device 060.

Figure 2:
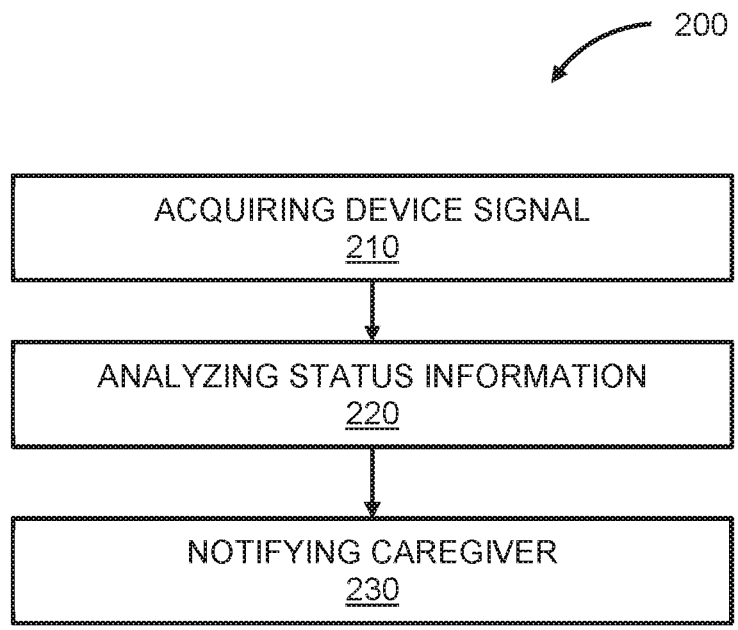
FIG. 2 shows a method for processing status information of a medical device.

FIG. 2 shows a method 200 for processing status information of a medical device which performs a medical function at a bedside of a patient and which is arranged for generating an alarm signal which is perceivable at the bedside of the patient to enable alerting a caregiver of the patient to an occurrence of an event which is associated with the performing of the medical function. The method 200 may correspond to an operation of the system 100. However, the method 200 may also be performed in separation of the system 100, e.g., using a different system. The method 200 comprises, in a first step titled "ACQUIRING DEVICE SIGNAL", acquiring 210 a device signal of the medical device, the device signal comprising status information which is indicative of a current status of the performing of the medical function. The method 200 further comprises, in a second step titled "ANALYZING STATUS INFORMATION", analyzing 220 the status information to estimate an imminent occurrence of the event based on said current status. The method 200 further comprises, in a third step titled "NOTIFYING CAREGIVER", notifying 230 the caregiver of the imminent occurrence of the event away from the bedside of the patient by a generating a notification signal for a notification device.

Figure 3:
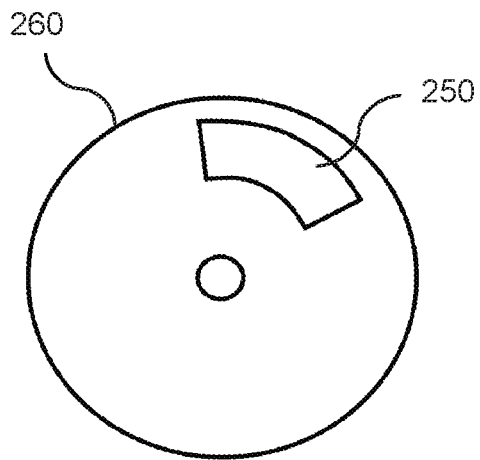
FIG. 3 shows a computer program product comprising instructions for causing a processor system to perform the aforementioned method.

FIG. 3 shows a computer program product 250 comprising instructions for causing a processor system to perform the aforementioned method 200. The computer program product 250 may be comprised on a computer readable medium 260, for example in the form of as a series of machine readable physical marks and/or as a series of elements having different electrical, e.g., magnetic, or optical properties or values.

Referring further to FIG. 1, the analysis subsystem 140 of the system 100 may estimate the imminent occurrence of the event from the status information of the device signal 024 in various ways. For example, if the status information in itself is highly indicative of the imminent occurrence of the event, the analysis subsystem 140 may estimate the imminent occurrence from the status information itself, i.e., without additional data. For example, if the status information denotes "INFUSION SPEED 0.2ML/S, REMAINING BAG VOLUME 120ML", the analysis subsystem 140 may estimate that the bag runs empty in 120 ml divided by 0.2 ml/s equals 600 seconds, so approximately in 10 minutes. If, on the other hand, the status information denotes "INFUSION STARTED AT 0.2ML/S" without denoting the remaining bag volume, the analysis subsystem 140 may consult interpretation data such as medical device specification to learn that the standard bag volume is 250 ML and therefore that the bag will run empty after approximately 21 minutes. Similarly, if the status information denotes "BATT LOW", the analysis subsystem 140 may consult the medical device specification to learn that the medical device 020 provides such warning if the battery time remaining is less than 20 minutes and that the medical device 020 will sound an alarm upon reaching a battery time of 10 minutes. Accordingly, the analysis subsystem 140 may determine that an event occurs in 10 minutes time for which the medical device 020 sounds an alarm, with the event being that the remaining battery time reaches 10 minutes.

Figure 4:
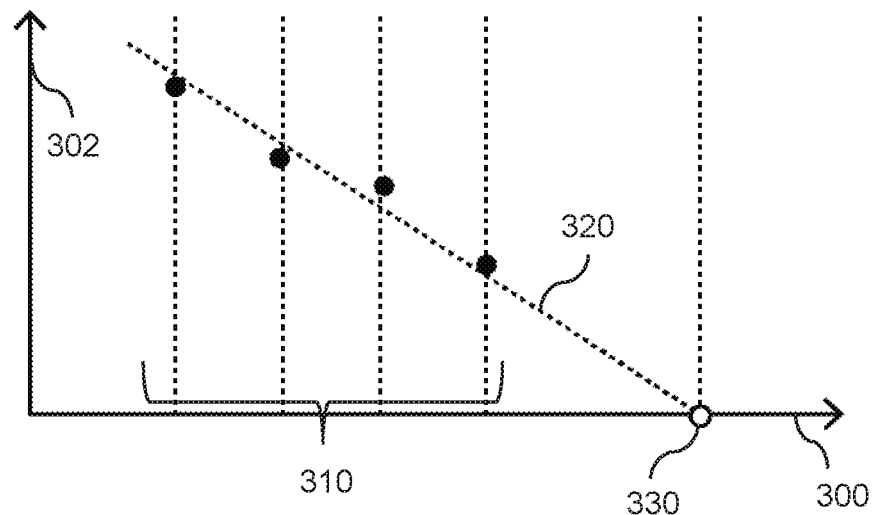
FIG. 4 schematically illustrates the estimating of the imminent occurrence of the event based on an extrapolation of a time series of status information.

The analysis subsystem 140 may also be arranged for tracking the status information over time to obtain a time series of status information. In addition, the analysis subsystem 140 may be arranged for estimating the imminent occurrence of the event by analyzing the time series of status information. In particular, the analysis subsystem 140 may extrapolate the time series of status information to estimate the imminent event. FIG. 4 schematically illustrates such an extrapolation. Here, a graph is shown which sets out, along a horizontal axis 300, the time, and along a vertical axis 302, a quantification of the status information. For example, if the status information relates to a current bag volume, the vertical axis 302 may represent said current bag volume in milliliters. FIG. 4 shows a time series of status information 310 which show a quantity decreasing over time. Here, a right-most one of the time series of status information 310 may represent a current status whereas the left-hand ones of the series of status information 310 may represent past statuses set apart by, e.g., 5 minute intervals. By extrapolating the time series of status information 310, the analysis subsystem 140 may determine an imminent event 330, namely in this example the bag volume reaching zero. In addition, the analysis subsystem 140 may estimate a time of the imminent occurrence of the event 330, namely in approximately 10 minutes time. Accordingly, the notification subsystem 160 may generate the notification signal 162 to notify the caregiver that the bag reaches empty in approximately 10 minutes time.

In general, the analysis subsystem 140 may be arranged for using reasoning techniques to estimate the imminent event based on the status information. For that purpose, the analysis subsystem 140 may or may not use interpretation data as knowledge base. It is noted that such reasoning techniques are known per se from the field of reasoning engines. Such interpretation data may be constituted by a set of pre-defined rules which enable the analysis subsystem 140 to estimate the imminent occurrence of the event by applying the rules to the status information. Another example of the interpretation data 044 is medical device information such as user manuals and medical data such as textbooks, guidelines, etc.

Referring further to FIG. 1, the status interface 120 may acquire the device signal 024 in various ways. For example, in case both the system 100 and the medical device 020 are connected to a local area network, the system 100 may obtain the device signal 024 in the form of a network message. The device signal 024 may be generated as part of an existing functionality of the medical device 020. For example, the medical device 020 may be arranged for interfacing with a server to deliver various status information to the server such as warnings, error messages, measurements, alarms, etc. An example of such status information includes technical status information, such as "BATT LOW" indicating that the estimated remaining battery-powered operating time is less than 20 minutes, as well as patient status information, such as "IRREGULAR HR" indicating that a consistently irregular cardiac rhythm has been measured. The device signal 024 may also take different forms. For example, the status interface 120 may obtain sensor data from a sensor such as a video camera. Such sensors may be directed at the medical device 020 to sense device signals such as visual warnings being displayed on a display of the medical device 020. For example, the status interface 120 may receive video data from a video camera of a closed-circuit television (CCTV) system within a hospital. The device signal 024 may be comprised in such sensor data in visual form, for example, in the form of as pixel data showing a display output of the medical device 020. The system 100 may be arranged for using a video or audio analysis technique to identify the device signal 024 in the sensor data and subsequently the status information from the device signal 024. Such techniques are known per se from the technical fields of image analysis and video analysis. For example, the system may use an image analysis technique to optically recognize characters of a visual warning on a display of the medical device 020, the visual warning constituting the device signal 024 from the medical device 020 and the characters together forming the status information.

Figure 5:
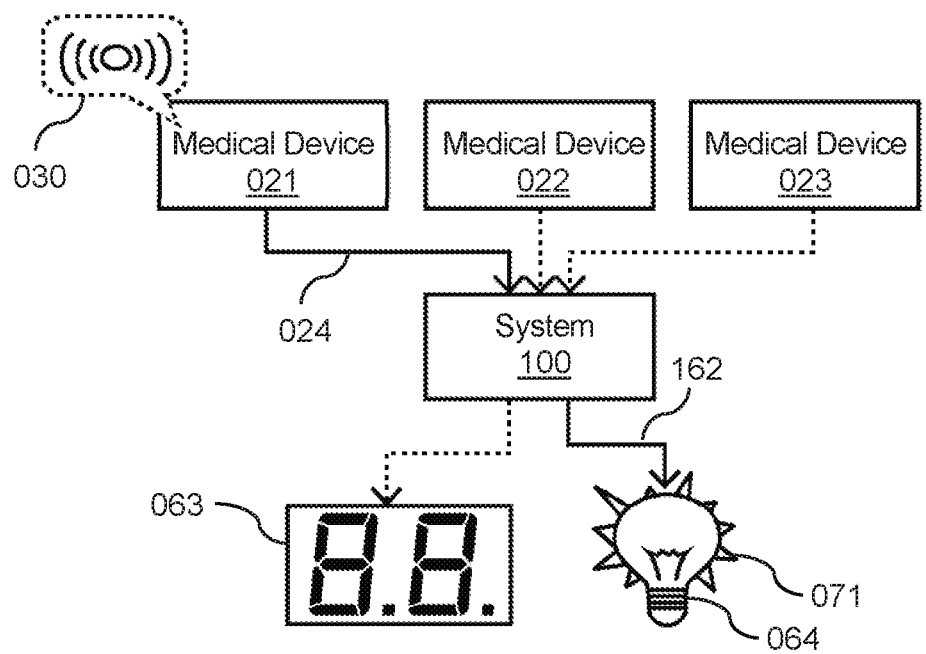
FIG. 5 shows the system generating the notification signal to effect a non-auditory notification of the caregiver via a segmented display or a light source.

Referring further to FIG. 1, the status interface 120 may be further arranged for acquiring physiological data 026 from a patient monitor 020 of the patient, and the analysis subsystem 140 may be arranged for estimating the imminent occurrence of the event further based on the physiological data. In FIG. 1, the medical device 020 is shown to be a patient monitor. Accordingly, the status interface 120 is shown to obtain both the device signal 024 as well as the physiological data 026 separately from the medical device 020. Alternatively, the physiological data 026 may also be provided as part of the device signal 024, e.g., by being included in the status information provided by the medical device 020. However, in case the medical device 020 is not a patient monitor but rather, e.g., an infusion pump, the status interface 120 may obtain the device signal 024 from the infusion pump while separately obtaining the physiological data 026 from a patient monitor of the patient. FIG. 5 shows the system 100 being arranged for processing status information from multiple medical devices 021-023. The multiple medical devices 021-023 may be multiple medical devices 021-023 of a same patient, of different patients or a combination thereof. FIG. 5 shows the system 100 receiving the device signal 024 from a first one of the medical devices 021, i.e., a first medical device 021. FIG. 5 further shows a callout box which is dashed to denote a possible future alarm signal 030 of the first medical device 021. In response to the status information of the device signal 024, the system 100 may generate the notification signal 162 for a notification device which is observable by the caregiver away from the bedside of the patient so as to notify the caregiver of the imminent occurrence of the event. FIG. 5 shows two different notification devices, namely a segmented display 063 and a light source 064. The notification subsystem 160 may be arranged for generating the notification signal 162 for either or both of said notification devices to effect a non-auditory notification of the caregiver. In the example of FIG. 5, the notification subsystem 160 is shown to generate the notification signal 162 for the light source 064, thereby causing the light source to generate a light signal 071. Accordingly, the caregiver obtains a visual notification when glancing at the light source 064. The light source 064 may, for example, be constituted by a patient call light which is located outside of the room of the patient, e.g., above a door to the room of the patient, thereby enabling the caregiver to easily associate the notification with the patient. The patient call light may switch on, change color, etc, to effect the notification to the caregiver. If a priority of the imminent occurrence of the event is known or estimated, the light source 064 may also reflect the priority, e.g., by changing color in a manner which mimics a traffic light. The segmented display 063 may be arranged at or near a nurse's station in the hospital. To enable the caregiver, i.e., a nurse, to easily associate a notification on the segmented display 063 with a patient, the notification subsystem 160 may generate the notification signal 162 to display a room number, a patient number, etc, on the segmented display 063. Another possibility is that the segmented display 063 may be arranged outside of the room of the patient where it provides a countdown timer to the estimated time of the imminent event.

Figure 6:
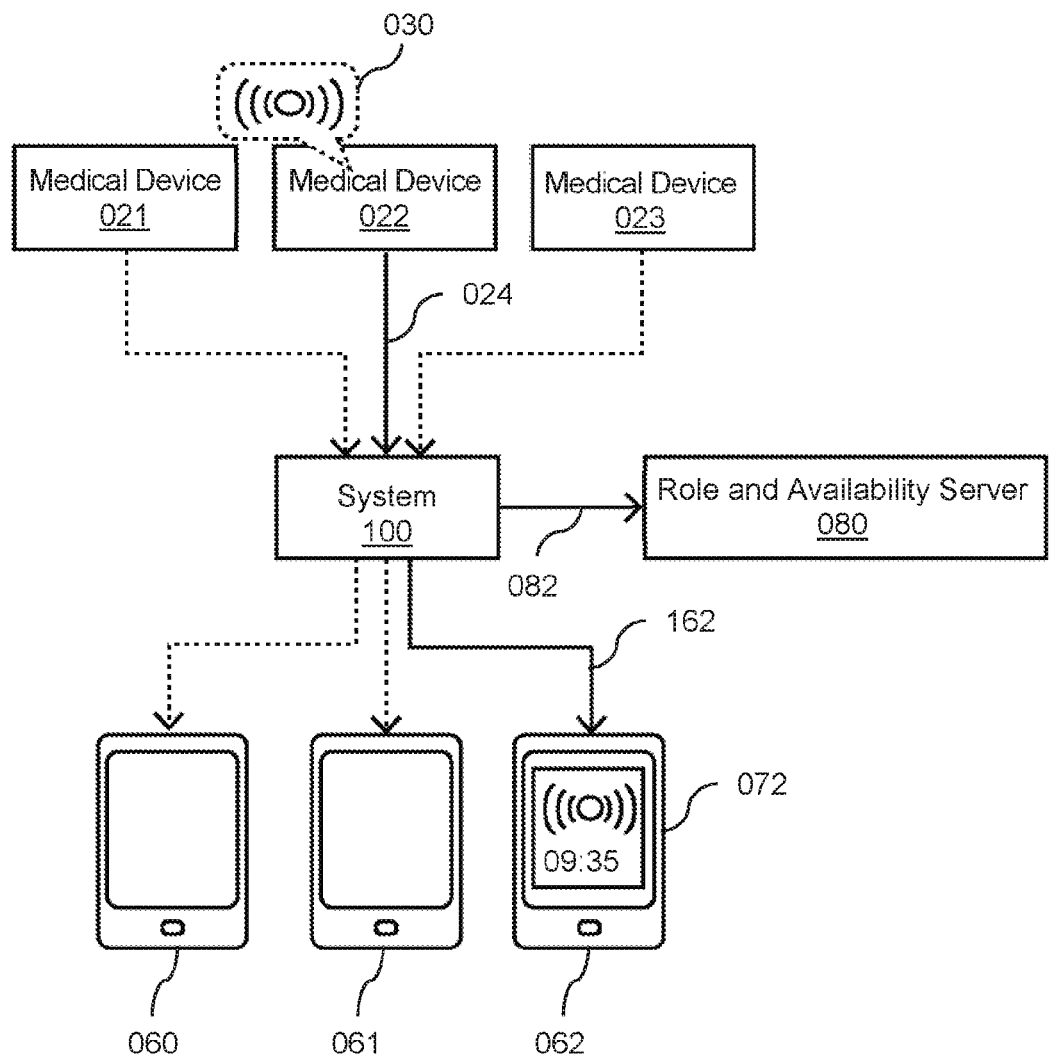
FIG. 6 shows the system using a role and availability server to determine which caregiver is to be notified of the imminent occurrence of the event.

FIG. 6 shows the system 100 making use of a role and availability server 080 to determine which caregiver is to be notified of the imminent occurrence of the event. Here, as in the example of FIG. 5, the system 100 is arranged for processing status information from multiple medical devices 021-023. FIG. 6 shows the system 100 receiving the device signal 024 from a second one of the medical devices 022, i.e., a second medical device 022. FIG. 6 further shows a callout box which is dashed to denote a possible future alarm signal 030 of the second medical device 022. In response to the status information of the device signal 024, the system 100 may generate the notification signal 162 for a notification device which is observable by the caregiver away from the bedside of the patient so as to notify the caregiver of the imminent occurrence of the event. The system 100 may be arranged for notifying one or more of a plurality of caregivers, namely by providing the notification signal 162 to a notification device of a particular caregiver. FIG. 6 shows three different mobile notification devices 060-062, in particular three different mobile phones, which each belong to a different caregiver. The notification subsystem 160 may be arranged for determining which caregiver to notify, and thus to which of the different mobile phones 060-062 to provide or route the notification signal 162, by consulting the role and availability server 080. The role and availability server 080 may indicate which caregiver is responsible and/or available to deal with the imminent occurrence of the event. The system 100 may, based on a data exchange 082 with the role and availability server 080, determine that the caregiver associated with a third one of the mobile phones 062, i.e., a third mobile phone 062, should be notified of the imminent occurrence of the event. Accordingly, the system 100 may provide the notification signal 162 to the third mobile phone 062. As a result, the particular caregiver is presented with a notification 072 showing a graphical representation of the alarm signal 030 and an estimated time of the imminent occurrence of the event, namely at 09:35. The notification subsystem 160 may thus route the notification to different caregivers depending on their role and/or availability.

Additionally or alternatively, the notification subsystem 160 may make use of location information to determine which caregiver to notify. Accordingly, the notification subsystem 160 may notify a caregiver which is closest by to the room of the patient. Such location information may be made available to the system 100, e.g., from these notification devices themselves if these are mobile devices, or from an external location tracking system.

In general, the notification subsystem 160 may be arranged for determining a priority of the notifying of the caregiver, and effecting the notifying of the caregiver based on the priority. For that purpose, the notification subsystem 160 may estimate whether the patient is asleep, and if the patient is estimated to be asleep, determine a higher priority than if the patient is estimated to be awake. The notification subsystem 160 may estimate whether the patient is asleep in various ways. For example, the notification subsystem 160 may analyze, or request the analysis subsystem 140 to analyze, physiological data as obtained from a patient monitor. For example, heart rate, breathing rate, SpO2 level, etc, may be analyzed to determine whether the patient is asleep or awake. Another example is that video analysis may be used to estimate whether the patient is asleep or awake from a video signal showing the patient. Yet another example is that the bed of the patient may be provided with load sensors, of which the sensor data may be analyzed. Yet another example is that the patient may be provided with a wrist-worn accelerometer device of which the sensor data may be analyzed. Additionally or alternatively, the notification subsystem 160 may make use of time data which indicates a time of day and/or light data which is indicative of an amount of light in a room of the patient. Such light data may be obtained from, e.g., a light sensor in the room of the patient or from a control system which indicates whether lights are turned on in the room of the patient. The notification subsystem 160 may also make use of information which indicates whether a television or similar device is turned on in the patient's room.

Based on priority, the notification subsystem 160 may effect the notifying in different ways. For example, the notification subsystem 160 may delay or discard the notifying if the priority does not exceed a threshold. Such notifications may also be presented to the caregiver as part of a schedule, i.e., be scheduled by the notification subsystem 160, the notification device and/or an external scheduling system. Accordingly, the priority as estimated by the notification subsystem 160 may determine a place in the schedule of the caregiver. For example, a low priority imminent event may be discarded or moved to a later time when the notification subsystem 160 determines that another imminent event has a higher priority. It will be appreciated that such scheduling may also be performed without determining the priority of the imminent event, e.g., by scheduling tasks in a worklist or tasklist of the caregiver which reflect the occurrence in time of each of the imminent events.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically.

Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for processing status information of a medical device performing a medical function at a bedside of a patient, the medical device being arranged for generating an alarm signal which is perceivable at the bedside of the patient to enable alerting a caregiver of the patient to an occurrence of an event which is associated with the performing of the medical function, the system comprising:
 a status interface for acquiring a device signal of the medical device, the device signal comprising status information which is indicative of a current status of the performing of the medical function;
 an analysis subsystem for analyzing the status information to estimate an imminent occurrence of the event based on said current status; and
 a notification subsystem for notifying the caregiver of the imminent occurrence of the event away from the bedside of the patient by a generating a notification signal for a notification device, the notification subsystem being arranged for i) determining a priority of the notifying of the caregiver based on estimating whether the patient is asleep, and ii) effecting the notifying of the caregiver based on the priority.

2. The system according to claim 1, wherein the notification subsystem is arranged for estimating whether the patient is asleep based on at least one of the group of: physiological data as obtained from a patient monitor, time data indicating a time of day, and light data being indicative of an amount of light in a room of the patient.

3. The system according to claim 1, wherein the notification subsystem is arranged for delaying or discarding said notifying if the priority does not exceed a threshold.

4. The system according to claim 1, wherein the analysis subsystem is arranged for i) tracking the status information over time to obtain a time series of status information, and ii) estimating the imminent occurrence of the event based on an extrapolation of the time series of status information.

5. The system according to claim 1, wherein the analysis subsystem is arranged for estimating a time of the imminent occurrence of the event, and wherein the notification subsystem is arranged for generating the notification signal to notify the caregiver of said time.

6. The system according to claim 1, wherein the status interface is further arranged for acquiring physiological data from a patient monitor of the patient, and wherein the analysis subsystem is arranged for estimating the imminent occurrence of the event further based on the physiological data.

7. The system according to claim 1, wherein the notification subsystem is arranged for generating the notification signal for a mobile notification device of the caregiver.

8. The system according to claim 1, wherein the notification subsystem is arranged for generating the notification signal for effecting a non-auditory notification of the caregiver.

9. The system according to claim 8, wherein the notification device comprises a light source, and wherein the notification subsystem is arranged for generating the notification signal for effecting the notification of the caregiver via the light source.

10. A medical device for performing a medical function at a bedside of a patient, the medical device being arranged for generating an alarm signal which is perceivable at the bedside of the patient to enable alerting a caregiver of the patient to an occurrence of an event which is associated with the performing of the medical function, the medical device comprising the system according to claim 1.

11. A method for processing status information of a medical device performing a medical function at a bedside of a patient, the medical device being arranged for generating an alarm signal which is perceivable at the bedside of the patient to enable alerting a caregiver of the patient to an occurrence of an event which is associated with the performing of the medical function, the method comprising:

acquiring a device signal of the medical device, the device signal comprising status information which is indicative of a current status of the performing of the medical function;

analyzing the status information to estimate an imminent occurrence of the event based on said current status; and notifying the caregiver of the imminent occurrence of the event away from the bedside of the patient by a generating a notification signal for a notification device, said notifying comprising i) determining a priority of the notifying of the caregiver based on estimating whether the patient is asleep, and ii) effecting the notifying of the caregiver based on the priority.

12. A computer program product comprising instructions for causing a processor system to perform the method according to claim 11.

* * * * *